(12) United States Patent
Xiao et al.

(10) Patent No.: US 6,406,873 B2
(45) Date of Patent: *Jun. 18, 2002

(54) PAI-2 AND T-PA AS DIAGNOSTIC MARKERS OF PERIODONTAL DISEASE

(75) Inventors: Yin Xiao, Brisbane; Clive L. Bunn, Wast Ryde; Peter M. Bartold, Sherwood, all of (AU)

(73) Assignee: Biotech Australia Pty Ltd, Roseville (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/237,260

(22) Filed: Jan. 26, 1999

Related U.S. Application Data

(60) Provisional application No. 60/072,601, filed on Jan. 26, 1998.

(51) Int. Cl.$^7$ ...................... G01N 33/543; G01N 33/573
(52) U.S. Cl. ...................... 435/7.92; 435/7.1; 435/7.4; 435/7.93; 435/7.94; 435/13; 435/23; 436/518
(58) Field of Search ...................... 435/7.1, 7.4, 7.8, 435/7.92, 7.93, 7.94, 7.95, 13, 23, 975; 436/518, 536, 69; 530/388.25, 388.26, 389.3

(56) References Cited

PUBLICATIONS

Birkedal–Hansen et al., "Matrix Metalloproteinases: A Review", Critical Rev. in Oral Biol. Med. 4(2):197–250 1993.*

Emeis et al., "Interleukin 1 and Lipopolysaccharide induce an Inhibitor of Tissue–type Plasminogen Activator in Vivo and in cultured endothelial Cells", J. Exp. Med. 163 pp. 1260–1266 1986.*

Laiho et al., "Enhanced Production and Extracellular Deposition of the Endothelial–type Plasminogen Activator Inhibitor in Cultured Human Lung Fibroblasts by Transforming Growth Factor–β", J. of Cell Biol. 103, pp. 2403–2410 1986.*

Mochan et al., "Interleukin 1 stimulation of plasminogen activator production in cultured ginival fibroblasts", J. Periodont Res. 23:28–32 1988.*

Van Hinsbergh et al., "Regulation of plasminogen activator production by endothelial cells: role in fibrinolysis and local proteolysis", Int. J. Radiat. Biol. 60:261–272, 1991.*

Oikawa et al., "Stimulation of Plasmin Activity in cultured human Fibroblast cells by Porphyromonas Endodontalis", Int. J. Biochem. 25:9, pp. 1227–1231, 1993.*

Deutsch et al., "Plasminogen: Purification from Human Plasma by Affinity Chromatography", Science 170:1095–1096 1970.*

Bartold et al., "Isolation and Characterization of Proteoglycans Synthesized by Adult Human Gingival Fibroblasts in Vitro" Archives of Biochemistry and Biophysics, 253, pp. 399–412 1987.*

Ogura et al., "Effects of Camplyobacter rectus LPS on plasminogen activator–plasmin system in human gingival fibrblast cells" J. of Period. Res. 30:132–140 1995.*

Naitoh et al., Localization of Urokinase–type Plasminogen Activator Inhibitor–1, 2 and Plasminogen in Colon Cancer J. Cancer Res. 86, 48–56 1995.*

Whawell et al., "Plasminogen activator inhibitor–2 expression in inflamed appendix", Histopathology 27, 75–78, 1995.

Sawdey et al., "Regulation of Murine Type 1 Plasminogen Activator Inhibitor Gene Expression in Vivo", J. Clin. Invest. 88:1346–1353, 1991.

Moller, "Structure and function of the urokinase receptor", Blood Coagulation and Fibrinolysis, 4:293–303 1993.

Lund et al., "Plasminogen activator inhibitor type 1: cell–specific and differentiation–induced expression and regulation inhuman cell lines, as determined by enzyme–linked immunosorbent assay", Mol. and Cell. Endoc. 60:43–53 1988.

Simpson et al., "Distribution of plasminogen activator inhibitor (PAI–1) in tissues", J. Clin. Pathol. 44:139–143 1991.

Andraesen et al., "Plasminogen activator inhibitors: hormonally regulated serpins", Mol. and Cell. Endocrinology 68:1–19, 1990.

Vassalli et al., "The Plasminogen Activator/Plasmin System", J. Clin. Invest. 88:1067–1072, 1991.

Kinnby et al., "Aggravation of gingival inflammatory symptoms during pregnancy associated with the concentration of plasminogen activator inhibitor type 2 (PAI–2) in gingival fluid", J. Periodont Res. 31:271–277.

Kinnby et al., "The plasminogen–activating system in gingival fluid from adults", Scand. J. Dent. Res. 102 334–41, 1994.

Kruithof et al., "Biological and Clinical Aspects of Plasminogen Activator Inhibitor Type 2", Blood 36 4007–4024, 1995.

(List continued on next page.)

Primary Examiner—Christopher L. Chin
Assistant Examiner—James L. Grun
(74) Attorney, Agent, or Firm—Foley & Lardner

(57) ABSTRACT

The existence and the extent of periodontal disease can be diagnosed by measuring plasminogen activator inhibitor 2 (PAI-2) and/or tissue plasminogen activator (t-PA) levels in gingival crevicular fluid (GCF). Levels of PAI-2 and t-PA in GCF rise sharply in the context of periodontal disease, and they also correlate with the severity of disease at different sites in the same patient.

15 Claims, 7 Drawing Sheets

OTHER PUBLICATIONS

Lecander et al., "Occurrence of a Specific Plasminogen Activator Inhibitor of Placental Type, PAI–2, in men and Non–pregnant Women" Fibrinolysis 3:27–30 1989.

Kruithof, "Plasminogen Activator Inhibitors—A Review", Enzyme 40:133–121 1988.

Uitto et al., "A Protease of Bacteroides gingivalis degardes cell surface and matrix glycoproteins of cultured gingival fibroblasts and induces secretion of collagenase and plasminogen activator", Infec. and Immunity 57:213–218, 1989.

Brown et al., "Molecular characterization of plasminogen activators in human gingival crevicular fluid", Arch. Oral Biol. 40:839–845, 1995.

Hamilton et al., "Contrasting effects of transforming growth factor–β and IL–1 on the regulation of plasminogen activator inhibitors in human synovial fibroblasts", J. of Immun. 151:5154–5164, 1993.

Saksela et al., Urokinase–type plasminogen activator and its inhibitor secreted by cultured human monocyte–

Wohlwend et al., "Plasminogen activator–specific inhibitors produced by human monocytes/macrophages", J. Exp. Med. 165:320–339, 1987.

Manchanda et al., "Lipopolysaccharide–induced modulation of human monocyte urokinase production and activity", J. of Immunology, 145:4174–4180, 1990.

Knudsen and Nachman, "Matrix plasminogen activator inhibitor", J. of Bio. Chem., 263:9476–9481, 1988.

Kumar and Baglioni, "Protection from tumor necrosis factor–mediated cytolysis by overexpression of plasminogen activator inhibitor type–2*", J. of Bio. Chem., 266:20960–20964, 1991.

Riedo et al., "Deacylated lipopolysaccharide inhibits plasminogen activator inhibitor–1, prostacylin, and prostaglandin $E_2$ induction by lipopolysaccharide but not by tumor necrosis factor–$2_1$", J. of Immun., 144:3506–3512, 1990.

Michel et al., "Moldulation of mRNA levels for urinary– and tissue–type plasminogen activator and plasminogen activator inhibitors 1 and 2 in human fibroblasts by interleukin 1", J. of Immun., 143:890–895, 1989.

* cited by examiner

PAI-2 AND T-PA AS DIAGNOSTIC MARKERS OF PERIODONTAL DISEASE

This application claims the benefit of U.S. Provisional Application No. 60/072,601 filed Jan. 26, 1998.

BACKGROUND OF THE INVENTION

Periodontal disease is possibly the most common disease known to man, and is said to affect three-quarters of the adult population. Loss of periodontal tissue due to periodontal disease is the principal cause of tooth loss in adulthood. Periodontal tissue loss may result from infectious disease (e.g., bacterially-induced gingivitis), nutritional disease, (e.g., scurvy), or neoplastic conditions. Typically, tissue loss is accompanied by inflammation, bleeding and ulceration. Without treatment, periodontal tissue loss loosens the tooth and ultimately may cause loss of the tooth and the alveolar bone tissue (periodontitis).

Gingivitis and periodontal disease cause enlargement of the periodontal pocket (gingival sulcus) of the affected tooth. The pocket observed in diseased gingiva is much deeper than the normal sulcus. This enlarged pocket is difficult to clean with either a tooth brush or floss and, consequently, bacteria and plaque accumulate within the pocket, causing further enlargement of the pocket. Eventually, the periodontal ligament and supporting alveolar bone are destroyed, leading to loss of the tooth.

To permit effective treatment of periodontitis, it is essential to identify the presence and severity of active periodontal disease within a periodontal pocket. Even deep periodontal pockets do not necessarily correlate with the presence of active periodontal disease and, accordingly, traditional methods of measuring pocket depth may not provide an accurate indicator of the progression of the disease. Clearly, a more accurate means of determining the presence and extent of active periodontal disease is greatly to be desired.

SUMMARY OF THE INVENTION

It therefore is an object of this invention to provide methods of diagnosing periodontal disease. It is a further object of the invention to provide kits for diagnosing periodontal disease.

In accomplishing the foregoing objects, there has been provided, in accordance with one aspect of the present invention, a method of diagnosing periodontal disease, comprising the steps of: (a) determining the level of a protein in individual gingival crevicular fluid (GCF) samples obtained from one of various sites of a patient, wherein said protein is selected from the group consisting of (i) tissue-type plasminogen activator (t-PA) and (ii) plasminogen activator inhibitor-2 (PAI-2); and (b) obtaining the mean level of said protein in the GCF and using the mean level to diagnose periodontal disease.

In accordance with another aspect of the invention, there is provided a method of diagnosing periodontal disease, comprising the steps of: (a) determining the level of a protein in individual gingival crevicular fluid (GCF) samples, each sample obtained from one of various sites of a patient, the protein selected from the group consisting of (i) tissue-type plasminogen activator (t-PA) and (ii) plasminogen activator inhibitor-2 (PAI-2); and (b) comparing the levels of the protein in the samples from the various sites, a statistically significant variation of the levels among the various sites indicating a diagnosis of periodontal disease.

In accordance with still another aspect of the invention, there is provided a method of diagnosing periodontal disease, the method comprising the steps of:

(a) determining the level of tissue-type plasminogen activator (t-PA) in individual gingival crevicular fluid (GCF) samples obtained from a plurality of sites of a patient; and (b) obtaining the mean of the level of t-PA in the GCF and using the mean level to diagnose periodontal disease. In one embodiment, the method may further comprise comparing the mean of the t-PA level in the GCF from the patient with a predetermined mean of the t-PA level in the GCF from a healthy individual, wherein a statistically significant increase of the mean level of the t-PA level in the GCF indicates the presence of periodontal disease.

In accordance with yet another aspect of the invention, there is provided a method of diagnosing periodontal disease, comprising the steps of: (a) determining the level of tissue-type plasminogen activator (t-PA) in individual gingival crevicular fluid (GCF) samples obtained from a plurality of sites of a patient; and (b) comparing the levels of t-PA in the samples from the various sites, wherein a statistically significant variation of the t-PA levels among the various sites indicates the presence of periodontal disease.

In accordance with still another aspect of the invention, there is provided a method of diagnosing periodontal disease, comprising the steps of: (a) determining the level of plasminogen activator inhibitor-2 (PAI-2) in individual gingival crevicular fluid (GCF) samples obtained from a plurality of various sites of a patient; and (b) obtaining the mean of the level of PAI-2 in the GCF and using the mean level to diagnose periodontal disease. In one embodiment, step (b) may further comprise comparing the mean of the PAI-2 level in the GCF from the patient with a predetermined mean level of PAI-2 in the GCF from a healthy individual, wherein a statistically significant increase of the mean of the PAI-2 level in the GCF indicates the presence of periodontal disease.

In accordance with a further aspect of the invention, there is provided a method of diagnosing periodontal disease, comprising the steps of: (a) determining the level of plasminogen activator inhibitor-2 (PAI-2) in individual gingival crevicular fluid (GCF) samples, each sample obtained from one of various sites of a patient; and (b) comparing the levels of PAI-2 in the samples from the various sites, wherein a statistically significant variation of the PAI-2 levels among the various sites indicates the presence of periodontal disease.

In accordance with yet another aspect of the invention, there is provided a method of diagnosing periodontal disease, comprising the steps of: (a) determining the level of tissue-type plasminogen activator (t-PA) and the level of plasminogen activator inhibitor-2 (PAI-2) in individual gingival crevicular fluid (GCF) samples obtained from a plurality of various sites of a patient; and (b) obtaining the respective mean of the t-PA levels and the PAI-2 levels in the GCF and using the mean levels to diagnose periodontal disease.

In one embodiment, the respective means of t-PA and PAI-2 levels in the GCF from the patient are compared respectively with predetermined means of the t-PA levels and the PAI-2 levels in the GCF from a healthy individual, wherein a statistically significant increase of both mean levels in the GCF indicates the presence of periodontal disease.

In accordance with a further aspect of the invention, there is provided a method of diagnosing periodontal disease, comprising the steps of: (a) determining the respective level of tissue-type plasminogen activator (t-PA) and plasminogen activator inhibitor-2 (PAI-2) in individual gingival crevicular fluid (GCF) samples obtained from a plurality of sites of a patient; and (b) comparing the t-PA levels of the various sites with each other, and the PAI-2 levels of the various sites with each other, where a statistically significant elevation of both the t-PA levels and the PAI-2 levels among the various sites indicates the presence of periodontal disease.

In a particular embodiment of each of the aspects of the invention described above, the GCF is collected locally from two or more sites of the patient. In another embodiment, the GCF is collected locally from sites selected from the group consisting of the mesial sites, and the buccal and labial sites on the lower teeth. In still another embodiment, the level of the compound is determined using an enzyme-linked immunosorbent assay. In a further embodiment, step (b) further comprises comparing the mean level of the protein in the GCF from the patient with a predetermined mean level of the protein in the GCF from a healthy individual, where a statistically significant increase of the mean level of the protein in the GCF indicates the presence of periodontal disease.

In accordance with still another aspect of the invention there is provided a diagnostic kit for detecting periodontal disease comprising: (a) at least one antibody that binds selectively to an antigen selected from the group consisting of (i) tissue-type plasminogen activator (t-PA) and (ii) plasminogen activator inhibitor-2 (PAI-2); (b) at least one control standard of a known concentration of the antigen; and c) a suitable container. In one embodiment, the kit further comprises a testing format capable of quantitatively determining the concentration of the antigen using the antibody. In another embodiment, the testing format of the kit is an enzyme-linked immunosorbent assay format. In still another embodiment, the kit further comprises a means for collecting gingival crevicular fluid locally. In a further embodiment, the means for collecting gingival crevicular fluid utilizes an absorbent material, preferably a filter paper.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF PREFERRED EMBODIMENTS

Figure 1:
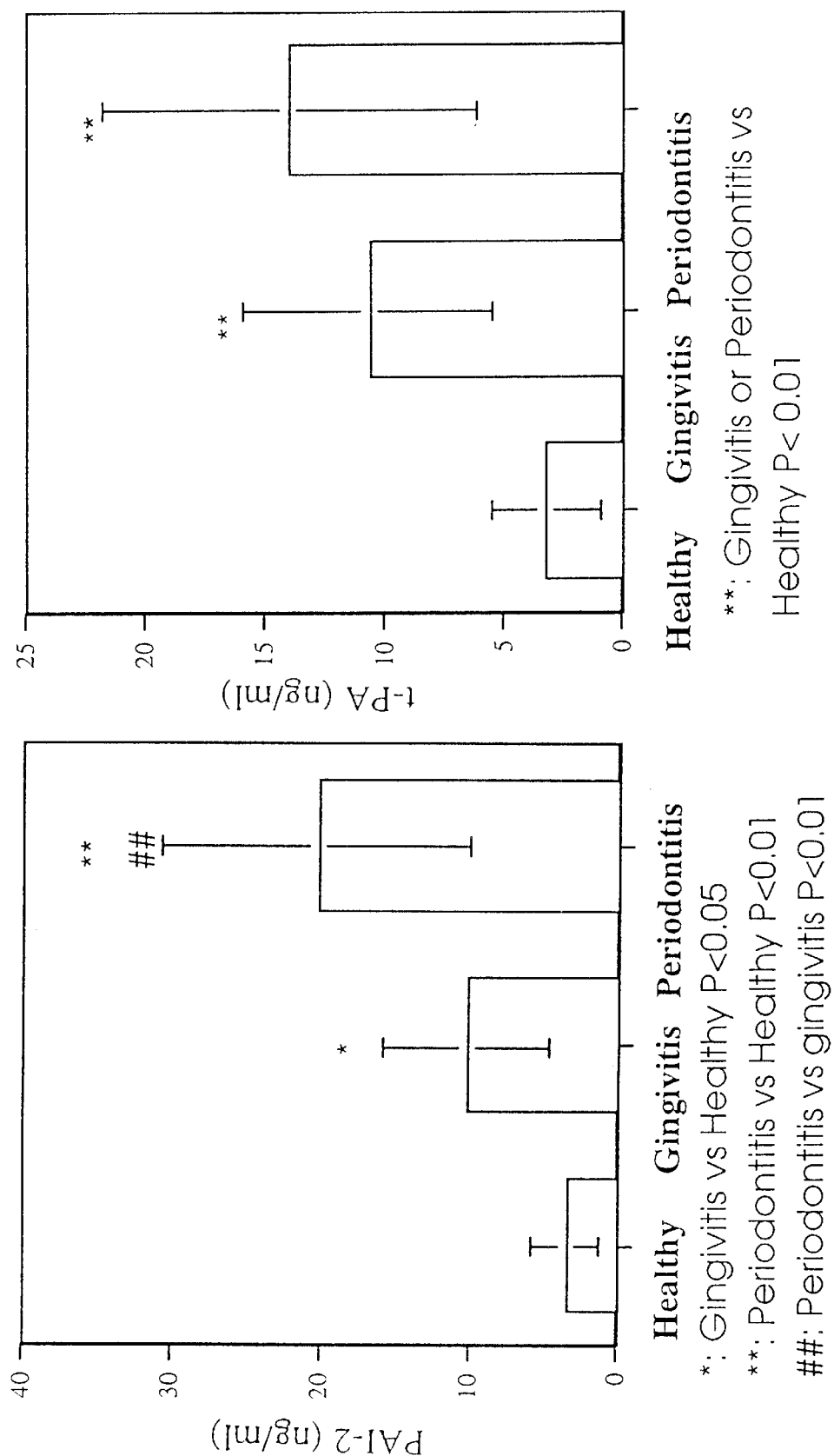
FIG. 1. Absolute amounts of t-PA and PAI-2(ng/ml/1 min) in GCF from healthy, gingivitis and periodontitis sites.

Methods for diagnosing periodontal disease by measuring levels of PAI-2 and/or t-PA in gingival crevicular fluid (GCF) are provided.

The invention is based upon the discovery that levels of PAI-2 and t-PA rise sharply in periodontal disease, decrease after treatment of the disease, and correlate with the severity of the periodontal condition. Accordingly, the existence and severity of periodontal disease can be diagnosed by measuring the levels of PAI-2 and t-PA in a patient's GCF. The processes of gingival inflammation, destruction of the periodontal connective tissues, and ultimate resorption of alveolar bone may be mediated by neutral proteases. Leukocytes, fibroblasts and bacteria have all been implicated as possible sources of the proteolytic enzymes Uitto, *J. Periodontol.* 54:740–745 (1983).

In many inflammatory-mediated conditions, the PA-plasmin proteolytic system has received considerable attention because of its participation in a wide variety of biological activities and in pathological conditions involving tissue destruction. Regulation of plasminogen activation is a key element in controlling proteolytic events in the extracellular matrix and this regulation is achieved through the action of specific plasminogen activator inhibitors. At sites of inflammation, the plasminogen activators/inhibitors system is involved in cell migration and tissue remodeling. Vassalli et al., *J. Clin. Invest.* 88:1067–1072 (1991). In particular, the plasmin-dependent pathway for activation of matrix metalloproteinases is considered to be a significant mechanism for the induction of matrix degradation. Birkedal-Hansen et al., *Crit. Rev. Oral biol. Med.* 4:197–250 (1993)

Plasminogen activators (PA) are serine proteases that convert plasminogen into plasmin, a trypsin-like serine protease, that not only is responsible for the degradation of fibrin, but also contributes directly and indirectly, via conversion of latent collagenase into active collagenase, to the degradation and turnover of the extracellular matrix Kruithof, *Enzyme* 40:113–121 (1988). Indeed, the plasmin-dependent pathway is understood to be a significant alternate pathway for the initiation of extracellular matrix degradation by matrix metalloproteinases. Birkedal-Hansen et al., supra.

Plasmin can be formed locally at sites of inflammation by limited proteolysis of its inactive precursor, plasminogen, which circulates in plasma and interstitial fluids. Deutsch et al., *Science* 170: 1095–1096 (1970). Plasminogen is activated by either urokinase-type plasminogen activator (u-PA) or tissue-type plasminogen activator (t-PA). These catalytic reactions generally take place at the plasma membrane (u-PA) or on a fibrin surface (t-PA). These activating enzymes are produced by a wide range of mesenchymal, epithelial and endoepithelial cells in response to a variety of cytokines and growth factors. Thus, at sites of inflammation, the potential for up- regulation of the plasminogen activating system is high. The resultant activated plasmin can degrade a wide range of substrates including extracellular matrix macromolecules (excluding collagens) and fibrin. The activities of plasmin and its activating proteinases are regulated extracellularly through a number of proteinase inhibitors including α2-macroglobulin, α1-proteinase inhibitor, α2-antiplasmin, plasminogen activator inhibitor-1 (PAI-1) and plasminogen activator inhibitor-2 (PAI-2). The regulation of PA activity by PA inhibitors (PAI) is also subject to hormonal regulation. Andreasen et al. *Mol. Cell. Endocrinol.* 68:1–19 (1990).

In its active form, PAI-1 is produced by endothelial cells and macrophages, and it specifically inhibits u-PA and t-PA activities. Andreasen et al., supra; Simpson et al., *J. Clin. Pathol.* 44:139–143 (1991). Furthermore, PAI-1 has been shown to be a component of extracellular matrix. Knudsen et al., *J. Biol. Chem.* 263:9476–948 (1988). This inhibitor may protect ECM constituents against cellular proteases and thus influence the cell migration and tissue destruction that occurs during development, inflammation and tumor metastasis. The activity of PAI-1 in cultured cells is regulated by a variety of hormones and cytokines, including dexamethasone (Lund et al., *Mol. Cell. Endocrinol.* 60: 43–53 (1988)), IL-1 (Emeis et al., *J. Exp. Med.* 163: 1260–1266 (1986)), TNFα (Sawdey et al., *J. Clin. Invest.* 88:1346–1353 (1991)) and TNF-β (Laiho et al., *J. Cell Biol.* 103:2403–2410 (1986)), and LPS (Ogura et al., *J. Peridont. Res.* 30:132–140(1995); Riedo et al., *J. Immunol* 144: 3506–3512 (1990)). These inflammatory mediators enhance the cell plasmin activity which may be dependent on their effects on PA-I.

The properties of PAI-2 are described in detail in Kruithof et al., Blood, 86:4007 (1995), which is hereby incorporated by reference. Briefly, PAI-2 is a component of a system that regulates extracellular proteolysis in a wide variety of physiological processes, such as tissue remodeling, cell migration, wound healing, and angiogenesis. See Kruithof, supra.

PAI-2 is produced in the placenta and by macrophages, and can be detected in the plasma of pregnant women but only rarely in the plasma of men and nonpregnant women. Lecander et al., *Fibrinolysis* 3:27–30 (1989). More recent studies suggest a wide tissue distribution of PAI-2. PAI-2 has been shown to be produced by a variety of cells in culture including monocyte/macrophage cell lines, fibroblasts and fibroblast-like cells, including fetal lung cells, foreskin, human synovial explants, and bone marrow stroma. The regulation of PAI-2 has been extensively studied in most of these cell lines. Basal PAI-2 expression is low or undetectable, but after suitable stimulation PAI-2 may be a major protein of cell extracts. Kruithof et al., supra. The expression of PAI-2 is regulated by a wide variety of factors including LPS (Whawell et al., *Histopathology;* 27: 75–78 (1995); Saksela et al., *J. Cell. Physiol.* 122:125–132 (1985)), TNF (Kumar et al., *J. Biol. Chem.* 266: 20960–20964 (1991)), interleukin-1 (Michel et al., *J. Immunol.* 143: 890–895 (1989)); Hamilton et al, *J. Immunol.* 151:5154–1561 (1993), and other cytokines and growth factors (Hamilton et al, *J. Immunol.* 151: 5154–1561 (1993)).

In human tissues, u-PA exists in several different forms including single-chain u-PA (scu-PA), high-molecular-weight u-PA (HMWu-PA), low-molecular-weight u-PA (LMWu-PA), u-PA/plasminogen activator inhibitor complex and as a u-PA/u-PA receptor complex. Naitoh et al., *Jpn. J. Cancer Res.* 86:48–56(1995); Moller et al., *Blood Coagulation and Fibrinolysis* 1993; 4:293–303 (1993).

The local overall activity of the plasminogen activator system depends upon the interaction between activators, plasminogen and inhibitors. Interaction of the different compounds depends on their relative topographic localization. Surprisingly, there have been relatively few studies addressing the presence and activity of the plasminogen activator system in inflamed periodontal tissues.

Distribution of plasiminogen activators and their inhibitors in gingival

The present inventors have studied the distribution of the plasminogen activators and their inhibitors PAI-1 and PAI-2 in human gingival fibroblasts, as well as in healthy and inflamed gingival issue. The results show that normal human gingival fibroblasts can express t-PA, u-PA and PAI-1. In addition, changes in the types of plasminogen activators present in healthy tissue and inflamed tissue are observed. For example, t-PA is significantly increased in connective tissue and u-PA is widely expressed in inflamed cells. The change of plasminogen activator inhibitors from healthy to inflamed tissue shows that PAI-1 and PAI-2 are widely expressed by inflamed cells and that some, but not all, fibroblasts express PAI-2.

Plasminogen activators may participate in the pathogenesis of periodontitis, and t-PA activity also may be a modulator of homeostasis of the periodontal connective tissues. Previous studies have shown high concentrations of t-PA in gingival crevicular fluid of inflamed gingival tissue and that the concentration of t-PA decreases after periodontal treatment. See Kinnby et al., *Scand. J. Dent. Res.* 102:334–41 (1994); Kinnby et al., *J. Periodont. Res.* 31:271–277 (1996); Brown et al., *Arch. Oral Biol.* 40:839–845 (1995). However, there is a lack of data on the site specific activity of t-PA and PAI-2 in the same periodontal patient, on comparisons of t-PA and PAI-2 levels among healthy, gingivitis and periodontitis groups, and on comparisons of t-PA and PAI-2 levels between before and after the treatment of periodontitis.

Furthermore, gingival fibroblasts can be stimulated by proteases from Bacteroides gingivalis and *Porphyromonas endodontalis* to secrete increased amounts of collagenase and plasminogen activator into their culture medium. Uitto et al., *Infect. Immun.* 1989; 57: 213–218; Oikawa et al., *Int. J. Biochem.* 1993:25:1227–1231. In addition, activated plasmin has been suggested to play a role in the progress of periodontal tissue inflammation through the activation of matrix metalloproteinases. Birkedal-Hansen et al., supra.

In vitro it has been shown that macrophages stimulate fibroblasts to activate plasminogen and that IL-I may stimulate gingival fibroblasts to produce PA activity. Mochan et al., *J. Periodontal Res.* 23:28–32 (1988). Moreover, endothelial cells can secrete t-PA on their luminal side where they may be exposed to IL-1. Van Hinsbergh et al., *Int. J. Radiat. Biol.* 60: 261–272 (1991). The present inventors have shown by immunocytochemical staining that t-PA localizes in cytoplasm of normal human gingival fibroblasts. This indicates that gingival fibroblasts may be a source of t-PA in connective tissues during the inflammatory period. The significant increase of t-PA in inflamed gingival connective tissue suggests that virulence factors from gram negative bacteria, such as lipopolysaccharide, may also be able to induce the expression of t-PA in connective tissue, which, in turn, then contributes to the destruction of periodontal tissue.

It is noteworthy that substantial amounts of u-PA have been shown to be present in gingival crevicular fluid, but no significant differences were noted between inflamed and healthy conditions. Kinnby et al., *Scand. J. Dent. Res.* 102:334–41 (1994). Possible sources of u-PA in the periodontal tissues include proliferating endothelial cells and macrophages. These cells have been shown to produce increased amounts of u-PA when appropriately activated in vitro. Manchanda et al., *J. Immunol.* 145:4174–80 (1990). Furthermore, gingival fibroblasts exposed to *Campylobacter rectus* LPS appear to release an increased amount of u-PA into their culture medium. Ogura et al., *J. Periodont. Res.* 30:132–140 (1995). The present inventors have shown that normal human gingival fibroblasts have a high intracellular u-PA expression. No difference was found in connective tissue expression of u-PA between healthy and inflamed gingival tissue.

The present inventors also have shown that normal gingival fibroblasts stain strongly for PAI-1, and that there is no difference in the expression of PAI-1 in connective tissue between healthy and inflamed gingival tissue. The broad distribution of PAI-1 throughout the gingival tissues suggests that PAI-1 represents the principal physiological inhibitor of t-PA and u-PA.

From the present study, there appear to be at least two potential sources for the PAI-2 found in gingival crevicular fluid: gingival fibroblasts and macrophages. In addition, activation of macrophages may also result in an increased production of PAI-2. Wohlwend et al., *J. Exp. Med.* 165: 320–339 (1987). The present inventors have determined the localization of PAI-2 in inflamed gingival tissue to be within inflammatory loci as well as clonally expressed by some fibroblasts. This may explain the deposition of fibrin during chronic inflammation.

PA/PAI can be detected in inflamed cell areas in inflamed gingival tissue which suggests that PA/PAI stored in the cytosol of monocytes and macrophages may represent a reservoir of PA/PAI activity that can be released at certain stages of the inflammatory reaction. It appears that the presence of such intracellular storage permits the immunohistochemical detection of PA/PAI in periodontal tissue.

The present inventors have shown, therefore, that the plasminogen activator system plays a significant role in connective tissue destruction associated with advancing periodontal inflammation.

Measurement of t-PA and PAI-2 levels in GCF

The present inventors also have shown that elevated concentrations of PAI-2 and/or t-PA in GCF are diagnostic for active periodontal disease, and that the relative levels of PAI-2 and/or t-PA correlate with the severity of the disease.

Methods for sampling GCF are well known in the art, and any method that reliably provides samples of GCF that are substantially uncontaminated by saliva may be used in the invention. Advantageously, GCF may be sampled using a sterile absorbent material, such as filter paper, that is placed in the gingival pocket for a predetermined period of time. The volume of the GCF absorbed onto the absorbent material can be determined by methods that are well known in the art, for example by using a Periotron 6000 (PRO FLOW Incorporated, New York). The GCF can be recovered from the absorbent material by buffer extraction, and the concentration of t-PA and PAI-2 determined.

Methods of determining the concentrations of particular proteins are well known in the art. For example, enzyme-linked immunosorbent assay (ELISA) may advantageously be used. The skilled artisan also will be aware of other methods for determining concentrations of t-PA and PAI-2. For example, t-PA is a serine protease with known characteristics with regard to substrate specificity, rate of catalysis, etc. and, accordingly, the concentration of t-PA may be measured using a standard enzymatic assay. Suitable assays are well known in the art.

Advantageously, GCF is collected from multiple gingival tissue sites (for example, 2–4 sites) in the same patient, allowing comparison of t-PA and PAI-2 levels between the different sites. Typically, prior to GCF collection, sites are assessed using standard clinical criteria, based upon probing depth (PD) and gingival index (GI). Sites that exhibit apparently similar levels of disease by these standard criteria can be compared. Elevated levels of t-PA and PAI-2 are found to correlate with the presence of active periodontal disease. In addition, it is found that significantly elevations in the mean concentrations of PAI-2 and t-PA in GCF from several sites correlate strongly with the presence of active disease.

GCF can be collected from any suitable gingival sites, although typically the mesial sites are used, as they were more accessible than distal sites. On the lower teeth buccal/labial sites are preferred to lingual sites as they are less prone to saliva contamination of the GCF sample during collection. Advantageously, collection sites are cleaned by removing the obvious supragingival plaque, for example with a curette, followed by carefully isolating the sites from saliva using a suitable physical barrier, for example, cotton rolls.

Diagnosis of the levels of active periodontal disease among different sites in the same patient can be made by a simple comparison of t-PA and/or PAI-2 concentrations at the different sites. Elevated t-PA and/or PAI-2 levels indicate active disease. Advantageously, comparison can be made with t-PA and PAI-2 levels in GCF collected from apparently clinically healthy tissue from sites in the same patient. Alternatively, the mean levels of t-PA and/or PAI-2 between several sites can be determined, and may be compared to a standard value. Typically, levels of t-PA and/or PAI-2 in clinically healthy patients are about 2–3 ng/ml, and in patients with gingivitis are about 4–5 ng/ml. By comparison, t-PA and PAI-2 levels are significantly higher in patients suffering from periodontal disease, for example 7–10 ng/ml. In the context of the present invention, t-PA and/or PAI-2 levels of about 7 ng/ml or above are considered to be diagnostic of the presence of active periodontal disease.

The present invention, thus generally described, will be understood more readily by reference to the following examples, which are provided by way of illustration and are not intended to be limiting of the present invention.

EXAMPLE 1

Analysis of t-PA, u-PA, PAI-1 and PAI-2 Expression in Gingival Tissue

A. Cell culture and cell immmunocytochemical staining

Human gingival fibroblasts were obtained by explant culture of healthy gingival tissue derived from healthy donors, as described by Bartold et al., *Arch. Biochem. Biophys.* 253:399–412(1987). Cells were maintained in Dulbecco's Modification of Eagle's Medium (DMEM) supplemented with 10% fetal calf serum (FCS), penicillin, streptomycin, glutamine, and non-essential amino acids at 37° C. in a moist atmosphere of 5% $CO_2$ and 95% air. Cells between the 5th and 8th passages in culture were used.

Glass cover slides for cell culture were autoclaved and placed in 4-well plates (Nunclon, Roskilde, Denmark). Cells were seeded into 4-well plates at an initial density of 20,000 cells per well and allowed to attach and spread on the cover slides for 24 to 48 hours in DMEM containing 10% FCS. The culture medium was removed and the cells were washed twice with PBS each for 5 minutes. After incubation for 10 hours in the presence or absence of 4 ng/ml of IL-1β (Immunex Corporation, Seattle, Wash.) in DMEM without FCS (6), the culture medium was removed and the cells were washed twice with PBS each for 5 minutes. All the cells were fixed in 4% paraformaldehyde for 20 minutes, then washed in PBS twice each for 5 minutes. The cell membranes were permeabilized for 12 minutes with 0.2% Triton X-100 (BDH Chemicals, Australia) in PBS, then washed in PBS twice each for 5 minutes.

Immunocytochemical staining was carried out as described below, using 5 μg/ml dilution of primary antibodies of t-PA, u-PA, PAI-1 and PAI-2.

B. Tissue preparation

Four patients (16 blocks of inflamed gingival tissue) and 2 healthy persons (6 blocks of healthy gingival tissue) were included in this study. The inflamed and healthy gingival sites were diagnosed on clinical and histological criteria in each case. The clinical selection criteria were based on treatment-based decisions and included specimens obtained from periodontal surgery for either management of sites with pocketing greater than 6 mm, persistent bleeding on probing and radiographic evidence of bone destruction and were non-responsive to conservative periodontal therapy (inflamed sites). Clinically non-inflamed tissue samples were obtained following crown lengthening surgery at sites with minimal loss of attachment, no bleeding on probing, and minimal radiographic evidence of bone loss. Histological assessment of the tissue specimens also was carried out and the presence or absence of significant inflammation was made on the basis of the presence of polymorphonuclear leukocytes and lymphocytes. While all specimens showed evidence of some inflammatory cell infiltration, the inflamed specimens were selected on the basis of greater than 50% of the tissues showing inflammatory cell infiltration while the healthy samples were selected on the basis of less than 5% of the tissue being infiltrated by these cells. All specimens were embedded in OCT-Tissue-Tek II (Miles Laboratories, Napierville, Ill., USA), snap frozen in liquid nitrogen, and store in liquid nitrogen. Cryostat sections (5 $\mu$m) were prepared, fixed in acetone, air-dried, and used for immunohistological staining.

C. Antibodies used for immunohistology

The following monoclonal antibodies were used for immunohistology. Monoclonal mouse anti-t-PA IgG (no. 104201; Biopool, Umea, Sweden) which binds to the A-chain in human tissue plasminogen activator. This antibody reacts moderately with human single-chain tissue plasminogen activator and the proteolytically modified two-chain tissue plasminogen activator. Monoclonal mouse anti-u-PA IgG (no. 3689; American Diagnostic) is directed against a B-chain epitope of human urokinase, near the catalytic site. This product reacts with free and receptor bound, single and two chain urokinase and the B-chain fragment. Monoclonal mouse anti-PAI-1 IgG (no. 3785; American Diagnostic) had been raised against purified active PAI-1 secreted by the human melanoma cell line. A monoclonal mouse anti-PA 1–2 IgG (Biopool, Umea, Sweden) was used which reacts with both the high molecular weight (60 kDa) form of PA 1–2 found in pregnancy plasma and with the low molecular weight (48 kDa) form of PAI-2 found in the placenta. This antibody also reacts with 2-chain t-PA/PAI-2 and u-PA/PAI-2 complexes but with lower affinity.

D. Immunohistochemical methods

All stages of the immunostaining procedures were carried out at room temperature. Prior to immunoperoxidase staining, endogenous peroxidase activity was quenched by incubating the tissue sections with 0.3% $H_2O_2$ for 20 minutes. All the sections were blocked by 1% bovine serum albumin (BSA) with 2% swine serum. Monoclonal antibodies to t-PA, u-PA, PAI-1 and PAI-2 were used at a dilution of 10 $\mu$g/ml in PBS and allowed to incubate for 60 minutes. After incubation with the primary antibodies, sections were rinsed with PBS solutions. Sections were then incubated with a biotinylated swine-anti-mouse, rabbit, goat antibody (DAKO Multilink, CA, USA) for 15 minutes, and then incubated with horseradish peroxidase-conjugated avidin-biotin complex (ABC) for 15 minutes. Antibody complexes were visualized after the addition of a buffered diaminobenzidine (DAB) substrate for 4 minutes. The reaction was stopped by immersion and rinsing of sections in PBS. Sections were then lightly counterstained with Mayer's haematoxylin and Scott's blue for 40 seconds each, in between 3 minute rinses with running water. Following this, they were dehydrated with ascending ethanol, cleared with xylene and mounted with a coverslip using DePeX mounting medium (BDH Laboratory Supplies, England).

Controls for the performance of the immunostaining procedures included conditions where the primary antibody or the secondary (anti-mouse IgG) antibody were omitted and a irrelevant antibody against a protein (membrane surface antibody CD15) which should not have been present in the test sections was used as a control.

To ensure that the procedure itself was not causing nonspecific staining, various safeguards were used. These included elimination of the primary antibody incubation step, in the presence of all other steps; and normal primary antibody incubation followed by elimination of either the secondary antibody or one of the other subsequent detection steps.

E. Evaluation Of Immunohistological Slide Preparations

Sections were viewed and photographically recorded using a Olympus System microscope (Model BX50, Tokyo, Japan). For the inflamed specimens, 16 consecutive sections were viewed and scanned by image analysis and for the non-inflamed specimens, 6 consecutive sections were subjected to analysis. The relative intensity of staining for the various tissue components in connective tissue was measured by image analysis (Computer Image System, NIH version 1.57). For each section three individual sites within the connective tissue (60 $\mu m^2$) were scanned and expressed as a reading per unit area. The difference between healthy and inflamed group was analyzed by Student's t-test. The significance level was set at $p<0.05$.

F. Results:

(i) Expression of plasminogen activators/inhibitors in cultured gingival fibroblasts In cultured gingival fibroblasts, t-PA, u-PA and PAI-1 are found to be expressed in the cytoplasm and concentrated around the nucleus. In particular, u-PA and PAI-1 stains strongly in these cells. Immunostaining for t-PA can be seen in cells but the staining intensity is low. Staining for PAI-2 is not detectable in normal gingival fibroblasts using the detection methods described below. When cells are treated with IL-1$\beta$, the staining for t-PA is increased and the expression of PAI-2 is expressed strongly in some single cells. There are no obvious differences in the staining of u-PA and PAI-1 in IL-1$\beta$ treated cells.

(ii) Staining for t-PA and u-PA in healthy and inflamed gingival tissue

In healthy tissue, t-PA stains weakly in the connective tissue. Fibroblasts and the cell matrix are mildly stained. In inflamed gingival tissue, the expression of t-PA in connective tissues is much stronger compared to healthy gingival tissues. All the fibroblasts and the cell matrix are intensely stained. Cytoplasmic staining in macrophages/monocytes is also observed for t-PA, but when compared with the staining in connective tissue, the distribution of t-PA is weaker in inflamed cells areas. The t-PA antigen is expressed very strongly around the blood vessels, especially in the endothelial cells in inflamed tissue. No t-PA staining is observed in normal and inflamed gingival epithelium.

A broad distribution for u-PA is observed in epithelium and connective tissue. The fibroblasts and cell matrix are weakly stained for u-PA in healthy gingival tissues. The staining in connective tissue is slightly increased in inflamed tissues. The u-PA antigen may be detected in a granular pattern in the cytoplasm of most macrophages/monocytes. The staining intensity is similar in healthy connective tissue and inflamed areas. Densitometric scanning of the sections confirms the visual assessment indicating that the staining for t-PA in connective tissue matrix is significantly increased (p<0.01) in inflamed tissue compare with the healthy tissue. Staining for u-PA in the connective tissue matrix is slightly increased but not significantly (p>0.05) in inflamed issue. The relative changes in levels of staining for plasminogen activators from healthy tissue to inflamed tissue are shown in Table I.

TABLE 1

Distribution of plasminogen activators/inhibitors in healthy and inflamed gingival tissues

|  | Epithelial | Connective tissue | Macrophages |
|---|---|---|---|
| Healthy tissue | | | |
| t-PA | − | + | |
| u-PA | + | + | |
| PAI-1 | + | + | |
| PAI-2 | + | − | |
| Inflamed tissue | | | |
| t-PA | − | +++ | + |
| u-PA | + | +++ | ++ |
| PAI-1 | + | +++ | ++ |
| PAI-2 | +++ | − | +++ |

Key:
−: no reactivity
+: faint or moderate reactivity
++: marked reactivity
+++: Strong marked reactivity (iii) Staining for PAI-1 PAI-2 in healthy and inflamed gingival tissue PAI-I is detectable immunohistochemically in healthy and inflamed gingival connective tissue. In healthy tissue, staining for PAI-1 is weak in the fibroblasts and extracellular matrix of the connective tissue. There is a slight increase in PAI-I staining in the connective tissue and a wider expression in the macrophage/monocytes in inflamed tissue.

In healthy tissue, no PAI-2 staining is observed in the connective tissue, whereas in inflamed tissue PAI-2 is predominantly localized to macrophages/monocytes and some fibroblasts. No obvious staining in the connective tissue cell matrix is seen. The epithelial staining is no different in either healthy or inflamed gingival tissues. See Table 1.

Generally, staining for PAI-1 and PAI-2 is widely expressed by inflammatory cells while some fibroblasts showed an elevated expression of PAI-2. Densitometric scanning of the stained sections indicates that there is a slightly increase in staining for PAI-1 in the connective tissue matrix, but this is not statistically significant (p>0.05) when compared with the inflamed tissue. No difference is found between PAI-2 in healthy and inflamed connective tissue matrix.

EXAMPLE 2

Analysis of t-PA and PAI-2 levels in GCF

A. Patient selection criteria 33 patients with different periodontal conditions were selected. These included 14 males and 19 females, aged from 20 to 55 years. No patients had received periodontal treatment or antibiotic therapy during the past half year. Ethical approval was obtained for the study and all patients gave informed consent to take part in the study. The subjects were assigned to a group on the basis of overall radiographic and clinical diagnostic criteria (healthy, gingivitis, and periodontitis). The clinic examination included measurements of probing depth (PD), gingival index (GI) and the evidence of alveolar bone loss by X-ray examination. GI score was based on the gingival appearance of redness and swelling and pocket bleeding on probing, scaled from 0–3, where 0 represents inflammatory free gingiva; 1 represents slight erythema and no bleeding on probing; 2 represents moderate erythema and bleeding on probing; 3 represents marked erythema and spontaneous bleeding tendency. The probing was performed after the sampling of GCF. The clinically healthy group had no overt signs of gingival inflammation or evidence of past disease and was defined by PD<2 mm, GI<1 and no sign of bone loss; gingivitis group was defined by PD<3, GI=1–2 and no sign of bone loss; periodontal group was defined by PD>3, GI>2 and obvious evidence of bone loss. In the healthy group, 20 sites were selected from 6 healthy patients for GCF collection; 17 sites were selected from 7 gingivitis patients for GCF collection in the gingivitis group; and 45 sites from 20 periodontitis patient were selected for GCF sampling in the periodontitis group. In addition, 24 sites from 11 periodontitis patients were selected according to the severity of the condition (PD>6 mm; GI>2) for further GCF analysis following periodontal treatment observation.

B. Gingival crevicular fluid (GCF) collection

In each patient, 2–4 sites were selected for GCF collection based on having the same clinical appearance (same GI, PD, and x-ray examination). The mesial sites were adopted for site selection as they were more accessible than distal sites. On the lower teeth buccal/labial sites were preferred to lingual sites as these sites were less prone to saliva contamination of the GCF sample. The collection sites were cleaned by removing the obvious supragingival plaque with a curette and the area was carefully isolated from saliva with cotton rolls, gently air dried. Sterile 2×10 mm strips of Whatman No. 1 filter paper (Whatman international Ltd, Springfield Mill, Maidstone, Kent, England) were inserted gently into the gingival crevice for 1 min. Care was exercised in order to avoid mechanical injury of the tissues. The volume of GCF on the paper strips was determined by Periotron 6000 (PRO FLOW Incorporated, New York) and the part of the strip containing the fluid sample was cut off and placed individually into a microcentrifuge tube containing 50 $\mu$l of Tris buffer (12 mM Tris, 0.1 M NaCl, 0.05% Tween 20). The samples were vortexed and stored at room temperature for 1 hour. The filter paper strip was discarded and the sample solution was frozen at −20° C. prior to analysis. The Periotron 6000 was calibrated with a 1 $\mu$l Hamilton syringe in the range of 0.1 $\mu$l to 1 $\mu$l in steps of 0.1 $\mu$l using distilled water. Each value was measured three times and the mean value for each volume was used in a linear regression analysis from which the slope and intercept were used to determine the volume of GCF collected.

C. Enzyme Immunoassay

Prior to analysis, the GCF samples were thawed at room temperature and vortexed. Each sample was assayed for t-PA and PAI-2.

t-PA antigen levels were measured using an enzyme linked immunosorbent assay (ELISA) kit: (IMUBIND total t-PA stripwell ELISA, American Diagnostics Inc., Greenwich) which is intended for quantitative determination of human tissue type plasminogen activator antigen. The immunoreactivities of single-chain and two-chain t-PA in complex with $\alpha$2-AP, PAI-1, and PAI-2 are 85% compared to non-complexed t-PA. Samples were applied in duplicate and the means of the absorbance values were used for the calibration of t-PA concentration.

Levels of PAI-2 antigen were measured on 20 $\mu$l samples with a standard sandwich ELISA kit developed at Biotech Australia. This assay uses rabbit polyclonal antibodies, and detects both glycosylated and non-glycosylated PAI-2, as well as PAI-2 complexed with u-PA or t-PA. A standard curve was determined using yeast recombinant human PAI-2, and was linear over the range of 1 ng/ml to 30 ng/ml.

Results were expressed as ng/ml/1 min sample. Control wells in each plate were included which contained no sample or standard antigen in order to calculate background binding.

D. Statistical analyses

The concentration of t-PA and PAI-2 was calculated, and mean values and standard deviations for each site diagnosed as exhibit healthy, gingivitis or periodontitis were determined. The clinical parameters were compared by means of an ANOVA test. Comparison within each group used an F test. Pearson's correlation coefficient method was used to compare the t-PA and PAI-2 levels with the clinical parameters of GCF volume, PD, and GI. A paired t-test was used to compare the difference of t-PA and PAI-2 before and after periodontal treatment. The statistically significant difference level was set at $p<0.05$.

E. Results

Samples from 106 sites in 33 patients were studied, the samples comprised 20 sites in 6 healthy patients, 17 sites in 7 gingivitis patients, 45 sites in 20 periodontitis patients, and 24 sites selected from 11 patients for periodontal treatment observation. FIG. 1 shows the amount (ng/ml/1 min) of t-PA and PAI-2 in GCF from healthy, gingivitis and periodontitis sites. The mean value for t-PA in GCF was significantly increased in the gingivitis and periodontitis sites compared with the healthy sites. The increase of PAI-2 in GCF was statistically significant in periodontitis sites compared with the healthy and gingivitis sites and also there was a significant increase in the gingivitis group compared with the healthy group.

Figure 2:
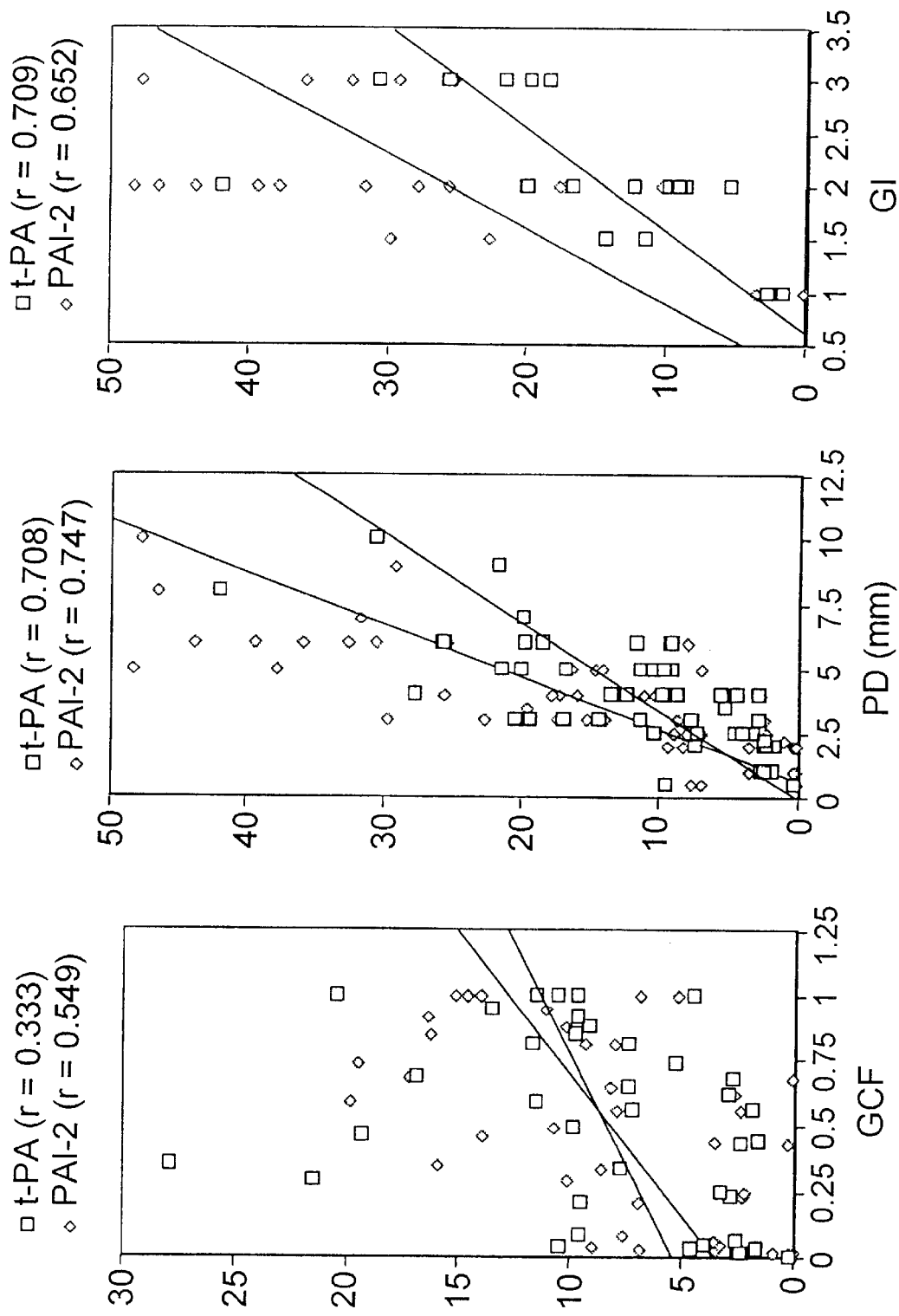
FIG. 2. Relationship between t-PA and PAI-2 levels in GCF from periodontal diseased sites to clinical parameters (GCF=Gingival crevicular fluid volume, PD=pocket depth; and GI=gingival index).

FIG. 2 shows the relationships between t-PA and PAI-2 levels in GCF from periodontal disease sites to clinical parameters such as GCF volume, PD and GI. The regression analysis showed there to be significant correlations between t-PA and PAI-2 in GCF with the clinic indexes such as GCF, PD and GI($P<0.05$). It is apparent from FIG. 2 that the levels of t-PA in GCF increased with the increased amount of GCF volume($r=0.33$, $P<0.05$), PD ($r=0.473$ $P<0.05$) and GI ($r=0.425$ $P<0.05$). A similar correlation was also observed between PAI-2 in GCF and GCF volume ($r=0.549$ $P<0.05$), PD($r=0.549$ $P<0.05$), and GI($r=0.592$ $P<0.05$), but the correlation coefficient for PAI-2 was slightly higher than t-PA.

Figure 3:
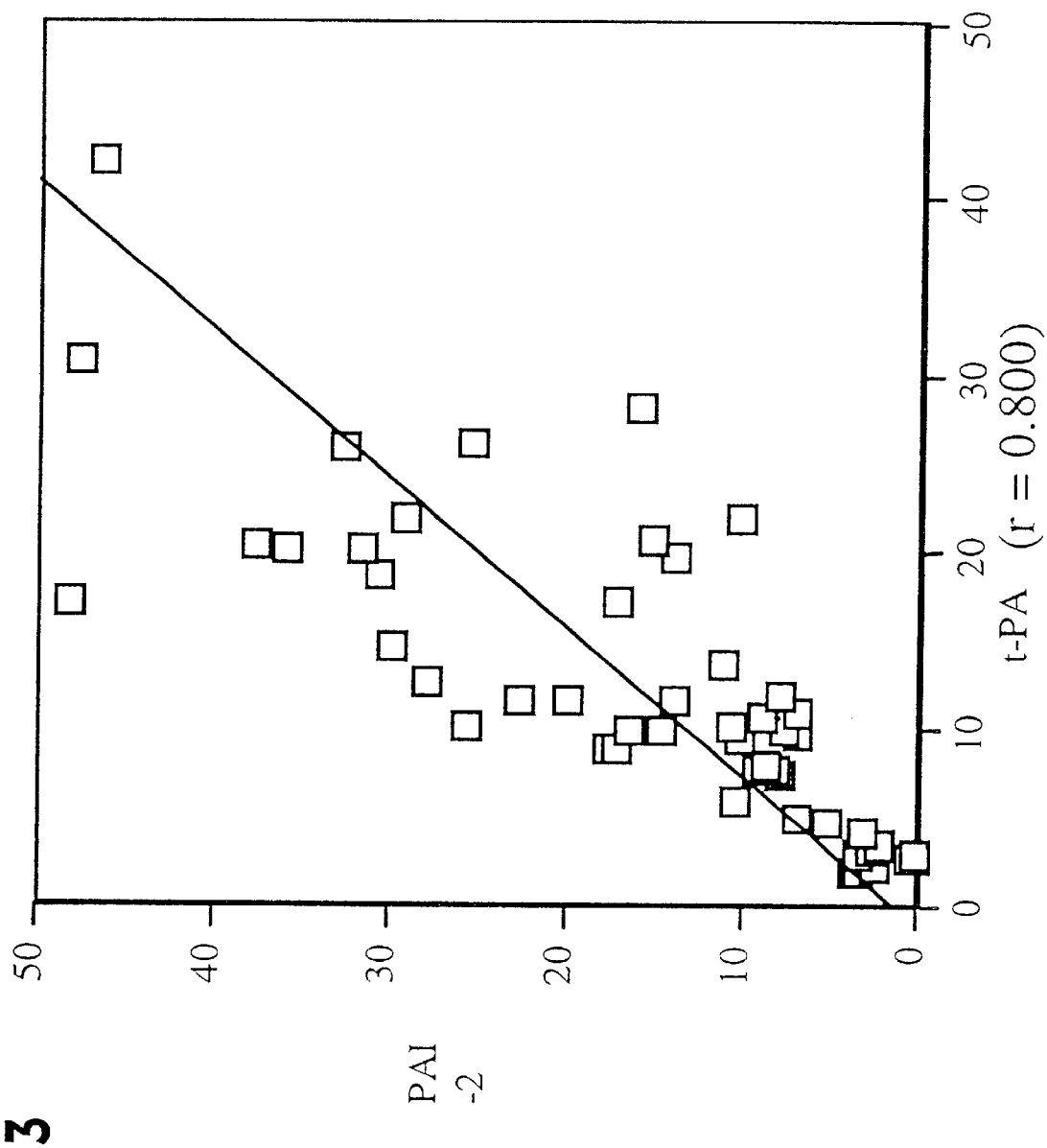
FIG. 3. Relationship between t-PA and PAI-2 levels on GCF.

FIG. 3 indicates the relationship between t-PA and PAI-2 levels in GCF. The results show that there was a significant correlation ($r=0.89$, $P<0.01$) between the level of t-PA and PAI-2 in GCF.

Figure 4:
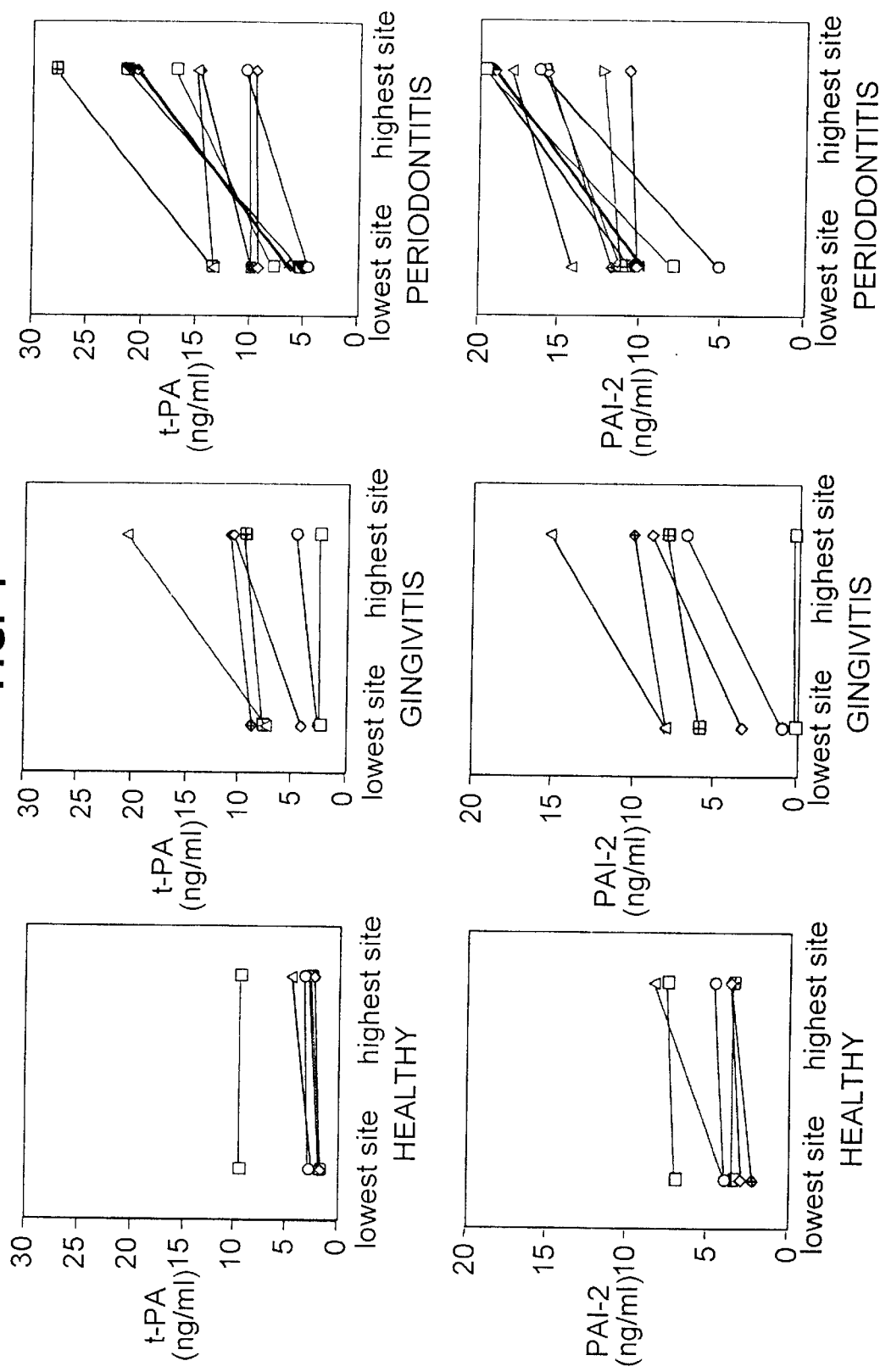
FIG. 4. Levels of t-PA and PAI-2 in GCF at different sites with the same disease status in the same patient from healthy, gingivitis and periodontitis groups.
Figure 5:
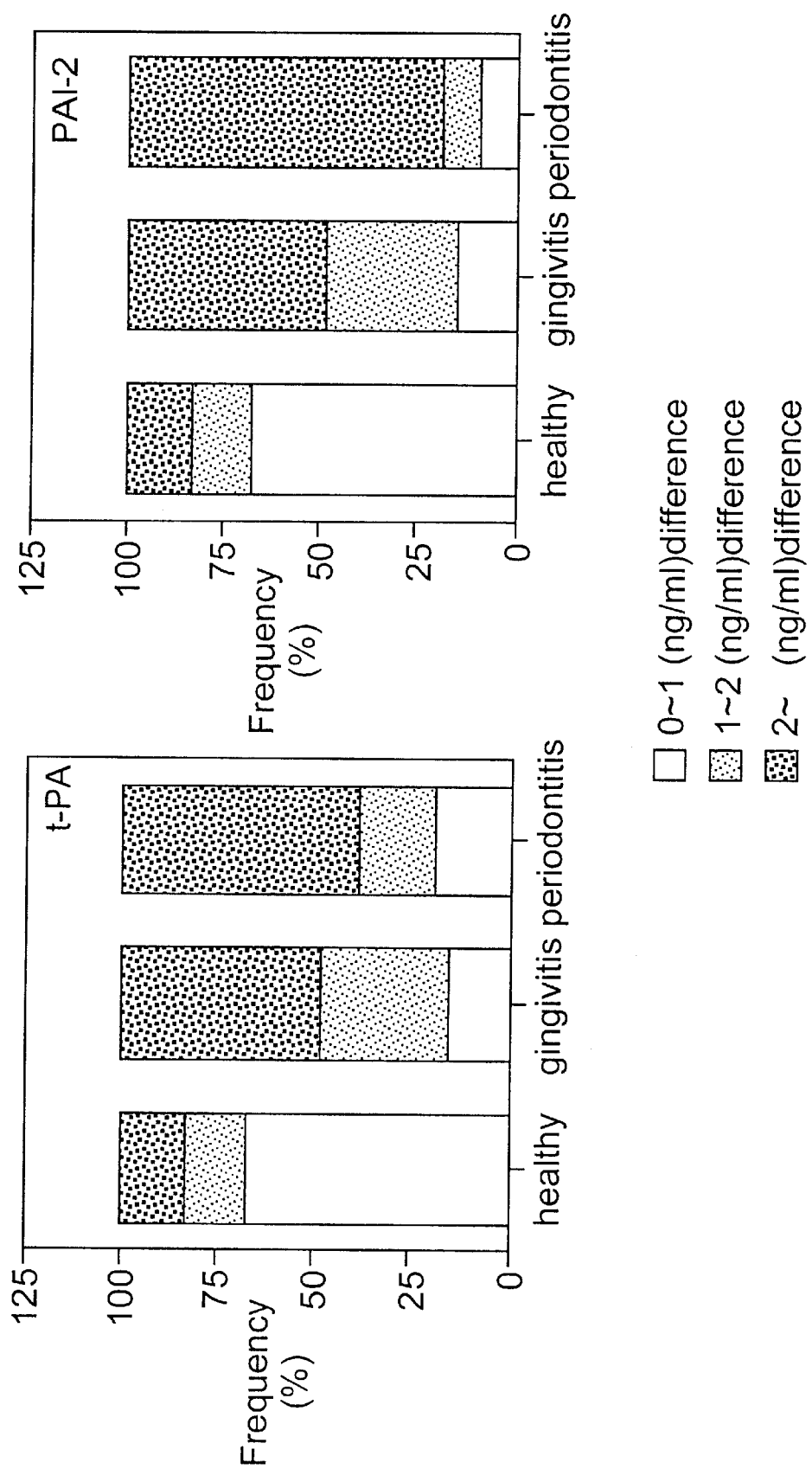
FIG. 5. Frequency variations of t-PA and PAI-2 in GCF at different sites with the same disease status in the same patient from healthy, gingivitis and periodontitis groups.
Figure 6:
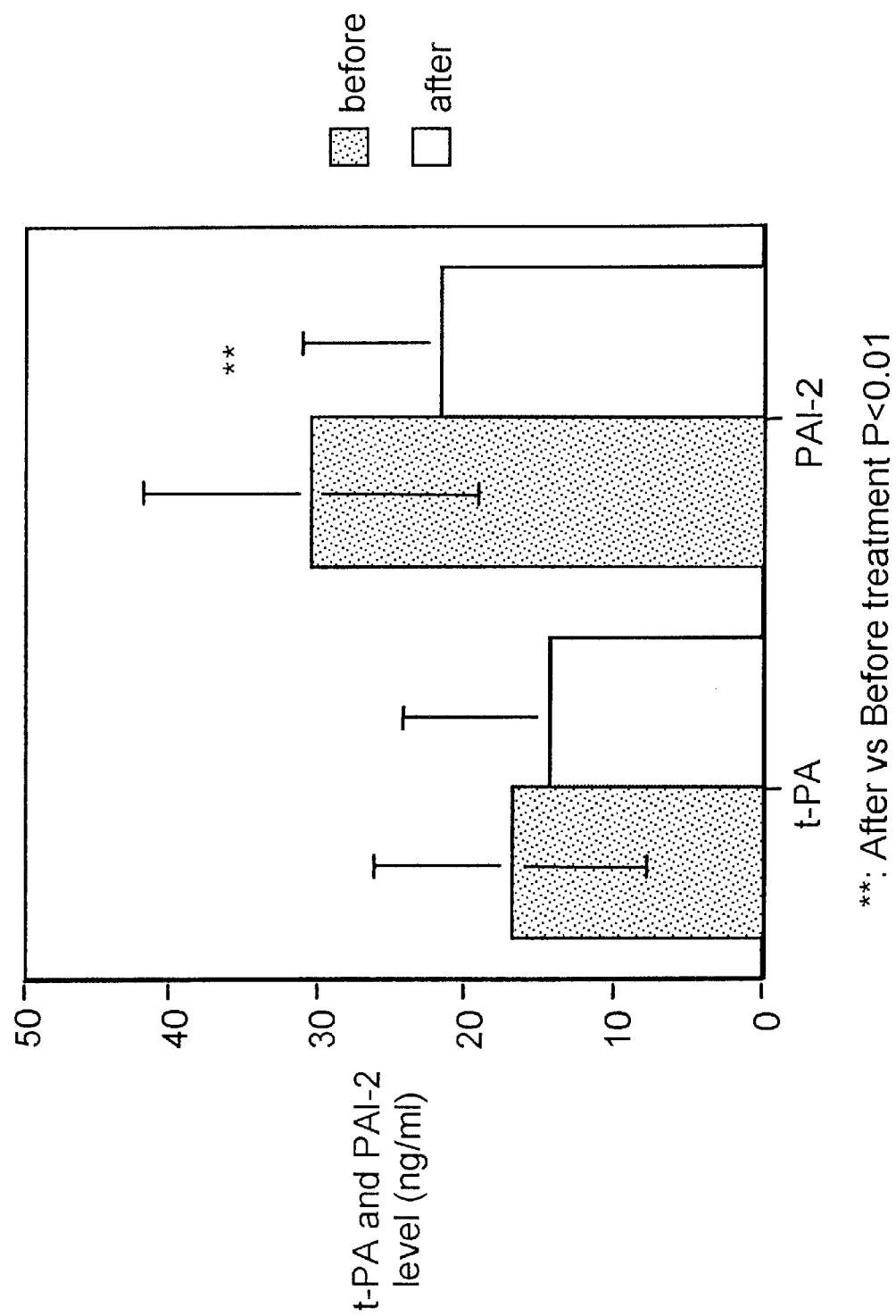
FIG. 6. Levels of t-PA and PA-2 in GCF two weeks after periodontal treatment.
Figure 7:
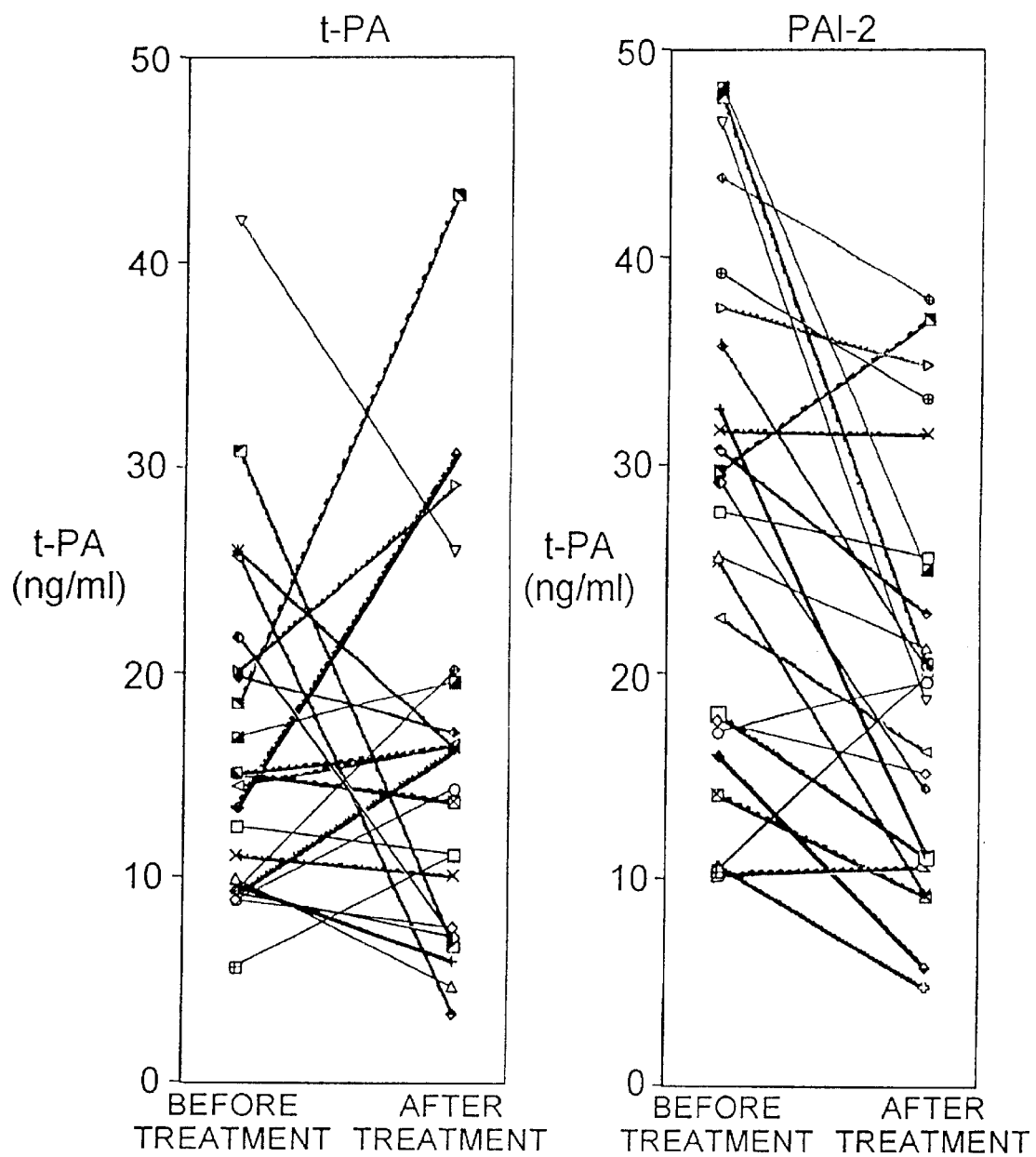
FIG. 7. Changes in t-PA and PAI-2 in GCF before and after two weeks of periodontal treatment.

FIG. 4 and FIG. 5 show the high and low activity levels of t-PA and PAI-2 in GCF at different sites disease status in the same patient from healthy, gingivitis and periodontitis group (FIG. 4) and their frequency variation (FIG. 5). In the clinically healthy sites, no obvious differences for the t-PA and PAI-2 levels in GCF between various sites of health in the same individual were noted. About 70% of the sites in the healthy group showed slight variations in the t-PA and PAI-2 levels (less than 1 ng/per site difference) between the high and low activity sites. In the gingivitis and periodontitis patients, there was considerable variation in the levels of t-PA and PAI-2 in GCF from different sites within the same patient. In the gingivitis group, 50% of the patients showed more than 2 ng/per site difference between the high and low activity sites and in the periodontitis group, more than 60% patients showed more than 2 ng/per site difference between the high and low activity sites. In 24 selected periodontitis sites which were subsequently treated, there was a significant decrease of PAI-2 in GCF two weeks after periodontal treatment (FIG. 6). In 19 sites (about 79%), the PAI-2 levels in GCF was decreased. The average amount of the decrease was 10±7.55, from 2.25 ng/ml to a maximum of 27.73 ng/ml (FIG. 7). In 3 sites 12.5%) the PAI-2 Levels in GCF increased and there was no change for 2 sites (7.5%) of PAI-2 in GCF (FIG. 7).

For t-PA levels, there was trend towards decreased levels in the GCF after two weeks of treatment, but the decrease was not statistically significant (FIG. 6). At 14 sites (59%) of the 24 selected periodontitis sites, t-PA in GCF decreased and 10 (41%) sites showed no change or even increased after 2 weeks of periodontal treatment (FIG. 7).

The invention has been disclosed broadly and illustrated in reference to representative embodiments described above. Those skilled in the art will recognize that various modifications can be made to the present invention without departing from the spirit and scope thereof.

What is claimed is:

1. A method of diagnosing periodontitis in a patient suspected of having periodontitis comprising the steps of:
   a) obtaining a plurality of individual gingival crevicular fluid (GCF) samples from the patient, wherein the samples are obtained from at least two different sites in the patient;
   b) determining a level of plasminogen activator inhibitor-2 (PAI-2) protein, or levels of each of PAI-2 protein and tissue-type plasminogen activator (t-PA) protein, in each of the individual samples;
   c) calculating a mean level for said PAI-2 protein or mean levels for each of said PAI-2 protein and said t-PA protein in said GCF samples; and
   d) comparing said mean level or levels with control level or levels, respectively, to detect an increase over control, wherein different degrees of said increase distinguish periodontitis from gingivitis in the patient.

2. The method of claim 1 wherein the level of the PAI-2 protein alone is determined in the samples.

3. The method of claim 2 wherein the level is determined with an enzyme-linked immunosorbent assay.

4. The method of claim 1 wherein the level of the PAI-2 protein and the level of the t-PA protein are determined in the samples.

5. The method of claim 4 wherein the levels are determined with protein-specific enzyme-linked immunosorbent assays.

6. The method of claim 1 wherein the samples are obtained from two to four different sites in the patient.

7. The method of claim 1 wherein the sites are selected from mesial, buccal, or labial sites on the lower teeth.

8. The method of claim 1 wherein the control level is a predetermined mean level of said PAI-2 protein or the control levels are predetermined mean levels of said proteins in GCF samples obtained from at least one healthy individual, and the increase of said mean patient level is or said mean patient levels are statistically significant as compared to the control level or levels, respectively.

9. A method of diagnosing periodontitis in a patient suspected of having periodontitis comprising the steps of:
   a) determining a level of plasminogen activator inhibitor-2 (PAI-2) protein in individual gingival crevicular fluid (GCF) samples, all said samples being obtained from a same single site of the patient;
   b) calculating a mean level for said PAI-2 protein in said GCF samples from said patient; and c) comparing said mean level with a control level to detect an increase over control, wherein different degrees of said increase distinguish periodontitis from gingivitis at the site.

10. The method of claim 9 wherein the site is selected from a mesial, buccal, or labial site on the lower teeth.

11. The method of claim 9 wherein the level of said PAI-2 protein is determined with an enzyme-linked immunosorbent assay.

12. The method of claim 9 wherein the control level is a predetermined mean level of PAI-2 protein in GCF samples obtained from at least one healthy individual and the increase of said mean patient PAI-2 level compared to the control level is statistically significant.

13. A method of diagnosing periodontal disease in a patient suspected of having periodontal disease, comprising the steps of:

a) determining levels of a protein in a plurality of individual gingival crevicular fluid (GCF) samples, each sample being obtained from a different one of various sites in the patient, the protein selected from the group consisting of (i) tissue-type plasminogen activator (t-PA) and (ii) plasminogen activator inhibitor-2 (PAI-2); and b) comparing the levels of the protein in the samples from the various sites in the patient, wherein a statistically significant variation of said levels indicates a diagnosis of periodontal disease in the patient.

14. The method of claim 13 wherein the protein is t-PA.

15. The method of claim 13 wherein the protein is PAI-2.

* * * * *